US010383777B2

(12) United States Patent
De Soto-Burt et al.

(10) Patent No.: US 10,383,777 B2
(45) Date of Patent: *Aug. 20, 2019

(54) VISUALLY PERCEPTIBLE TAMPON HOUSED WITHIN AN APPLICATOR

(71) Applicant: The Procter & Gamble Company, Cincinnati, OH (US)

(72) Inventors: Widalys Luz De Soto-Burt, Cincinnati, OH (US); Nanda Christine Almond, Walton, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/289,457

(22) Filed: Oct. 10, 2016

(65) Prior Publication Data

US 2017/0020743 A1 Jan. 26, 2017

Related U.S. Application Data

(63) Continuation of application No. 14/014,624, filed on Aug. 30, 2013, now abandoned.

(51) Int. Cl.
*A61F 13/15* (2006.01)
*A61F 13/20* (2006.01)
*A61F 13/26* (2006.01)

(52) U.S. Cl.
CPC .......... *A61F 13/2077* (2013.01); *A61F 13/26* (2013.01); *A61F 13/266* (2013.01)

(58) Field of Classification Search
CPC ..... A61F 13/2077; A61F 13/26; A61F 13/266

(Continued)

(56) References Cited

U.S. PATENT DOCUMENTS

| 4,536,178 A * | 8/1985 | Lichstein | A61F 13/26 |
| | | | 604/15 |
| 6,258,075 B1 * | 7/2001 | Taylor | A61F 13/2051 |
| | | | 604/385.18 |

(Continued)

FOREIGN PATENT DOCUMENTS

WO WO-2008/135925 A1 11/2008

OTHER PUBLICATIONS

PCT International Search Report, dated Oct. 28, 2014, 157 pages.

*Primary Examiner* — Michele M Kidwell
(74) *Attorney, Agent, or Firm* — William E. Gallagher

(57) ABSTRACT

The present disclosure is directed to a hygiene device including an applicator housing a tampon. The tampon can include a primary absorbent member having a leading end, a trailing end opposite the leading end, and an intermediate region. The primary absorbent member can include a first tampon color. The tampon can also include a secondary absorbent member which is mechanically tied to the primary absorbent member. The secondary absorbent member can include a second tampon color. The tampon can further include a withdrawal member disposed on at least one of the secondary absorbent member and the primary absorbent member. The withdrawal member can include a third tampon color. The applicator can include an insertion portion that includes an opaque region and a plunger operatively engaged with the insertion portion. The plunger can have a transparent region such that at least one of the secondary absorbent member and the withdrawal member is visually perceptible through the applicator.

15 Claims, 9 Drawing Sheets

(58) Field of Classification Search
USPC .............................. 604/385.17, 385.18, 904
See application file for complete search history.

(56) References Cited

U.S. PATENT DOCUMENTS

| | | | |
|---|---|---|---|
| 6,302,861 B2* | 10/2001 | Tweddell, III | A61F 13/2051 604/15 |
| 7,815,594 B2 | 10/2010 | Dougherty et al. | |
| 8,062,245 B2 | 11/2011 | Gann et al. | |
| 2003/0176845 A1* | 9/2003 | Kollwitz | A61F 13/2031 604/385.17 |
| 2005/0055003 A1 | 3/2005 | Bittner et al. | |
| 2007/0016156 A1* | 1/2007 | Burgdorf | A61F 13/202 604/385.18 |
| 2008/0275418 A1 | 11/2008 | Hughes et al. | |
| 2010/0000897 A1 | 1/2010 | Bumpass et al. | |
| 2010/0193386 A1 | 8/2010 | Loyd et al. | |
| 2012/0101424 A1* | 4/2012 | Watanabe | A61F 13/26 604/18 |
| 2012/0127663 A1 | 5/2012 | Mochizuki et al. | |
| 2012/0283684 A1 | 11/2012 | Schmidt-Foerst et al. | |
| 2015/0060317 A1 | 3/2015 | De Soto-Burt et al. | |
| 2015/0065942 A1 | 3/2015 | De Soto-Burt et al. | |
| 2015/0223993 A1 | 8/2015 | Ito et al. | |

* cited by examiner

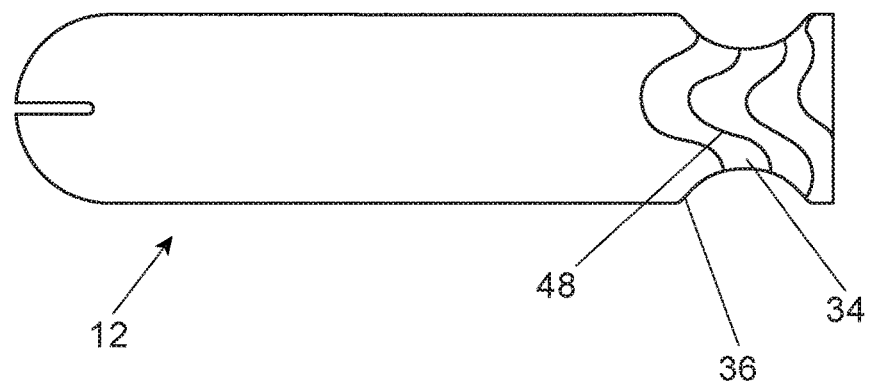
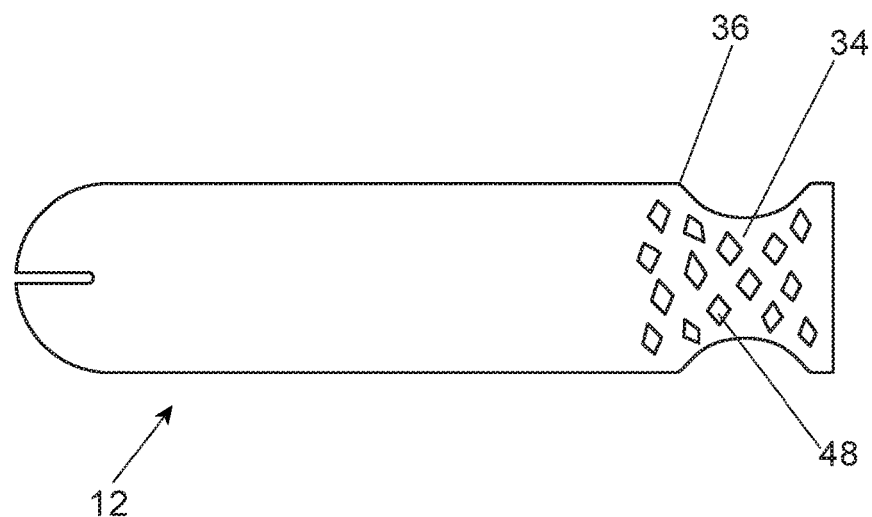
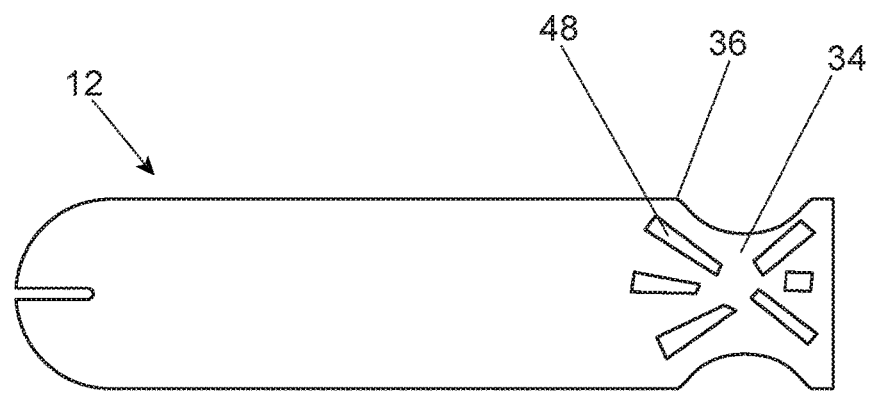

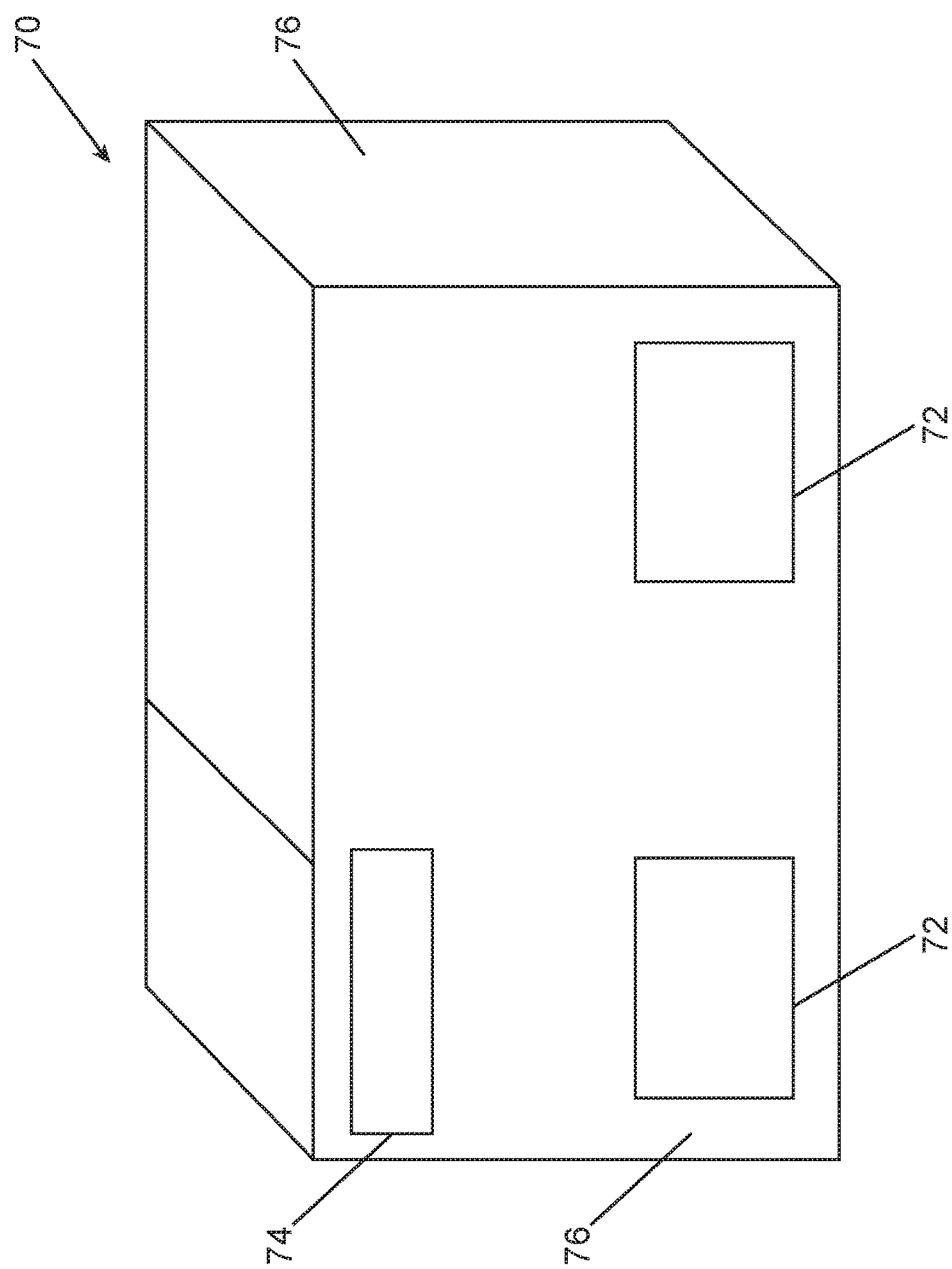

VISUALLY PERCEPTIBLE TAMPON HOUSED WITHIN AN APPLICATOR

FIELD OF THE INVENTION

The present disclosure relates to an improved feminine hygiene device, and more particularly, to an improved applicator housing a tampon, wherein the tampon is visually perceptible through the applicator to signal increased protection and correct application and/or to invoke happiness.

BACKGROUND OF THE INVENTION

Feminine hygiene devices, such as tampons and pessaries, are generally used by women within the vagina for feminine needs, such as, for example, to absorb menstrual or other body exudates, for pelvic support, and/or for other feminine needs. Such feminine products can be inserted into the vagina digitally or using an applicator.

Applicators typically comprise an insertion portion and a plunger. The material to be expelled from the applicator, such as an absorbent tampon or pessary, can be positioned within the insertion portion. To use the applicator, the consumer can grasp the insertion portion, position the insertion portion appropriately, such as, for example into the body, and move the plunger into the insertion portion towards the insertion end to insert the material, such as a tampon.

A variety of absorbent tampons have been used in applicators that perform their intended function of addressing feminine needs. Most currently available tampons are made from a pledget which is compressed into a cylindrical form. The compressed tampon can then be housed in the applicator for insertion. Post insertion, the tampon can absorb fluids, for example. Most tampons perform the function of fluid absorption and leakage prevention fairly well. Nevertheless, it has been recognized that fluids can travel the length of the vagina and fail to interact with the tampon. A tampon has been developed that includes a secondary absorbent member to capture those fluids that have bypassed the tampon.

However, consumers are largely unaware of the added protection provided by the secondary absorbent member. The secondary absorbent member resides at the trailing end of the primary absorbent member. Thus, when the tampon is housed within the applicator, the consumer has no visual indication that the secondary absorbent member exists and, further, is unable to fully appreciate the benefits that the secondary absorbent member can deliver. Accordingly, a need exists for an applicator in combination with a tampon comprising a secondary absorbent member where the consumer can visually identify and perceive the secondary absorbent member.

It has also been found that consumers desire some indication that the applicator has been appropriately configured and that the applicator including the tampon is in proper placement for insertion. For example, those consumers with little or no experience with feminine hygiene devices can become easily intimidated and overwhelmed with excessively complex devices or devices in which there is no confirmation of correct configuration of the device. More specifically, inexperienced consumers may be concerned that the plunger is not fully deployed or that the withdrawal string is not appropriately positioned for post use removal.

It has been found that consumers often experience uncomfortable symptoms when menstruating. More specifically, consumers can experience mood swings, cramps, headaches, and fatigue. This often results in consumers feeling melancholy. The currently available hygiene devices have largely failed to address these consumer feelings. More specifically, tampons have generally been available in a completely white color scheme and the applicator, which houses the tampon, has provided only minimal color to the hygiene device. Further, the consumers are largely unable to view any portion of the tampon within an applicator and generally, applicators have been designed to have opaque, single color housings that fail to provide a technical solution that delivers an emotional and/or aesthetic benefit to the consumer. Thus, a need exists for a package of products that provides some emotional and functional benefit to consumers. Likewise, it would be beneficial for manufacturers of hygiene products to be able to incorporate surprise and excitement into their products both individually and as a package of two or more products.

SUMMARY OF THE INVENTION

One embodiment of the present disclosure is directed to a hygiene device including a tampon and an applicator housing the tampon. The tampon can comprise a primary absorbent member comprising a leading end, a trailing end opposite the leading end, and an intermediate region between the trailing end and the leading end. The primary absorbent member can have a first tampon color. The tampon can also comprise a secondary absorbent member which is mechanically tied to the primary absorbent member. The secondary absorbent member can have a second tampon color. The tampon can also comprise a withdrawal member disposed on at least one of the secondary absorbent member and the primary absorbent member and extending from the secondary absorbent member in a direction substantially parallel to a longitudinal tampon axis. The withdrawal member can have a third tampon color. The applicator can comprise an insertion portion which includes an opaque portion and a plunger operatively engaged with the insertion portion. The plunger can include a first component comprising a transparent region such that at least one of the secondary absorbent member and the withdrawal member is visually perceptible through the first component, and a second component slidably engaged with the first component.

Another embodiment of the present disclosure is directed to a hygiene device comprising a tampon and an applicator housing the tampon. The tampon can comprise a primary absorbent member comprising a leading end, a trailing end opposite the leading end, and an intermediate region between the trailing end and the leading end. The tampon can also include a secondary absorbent member that is mechanically tied to the trailing end of the primary absorbent member, and a withdrawal member disposed on at least one of the secondary absorbent member and the primary absorbent member. The applicator housing the tampon can comprise an insertion portion that includes an opaque portion and a plunger operatively engaged with the insertion portion. The plunger can include a transparent region configured to visually perceive at least a portion of the secondary absorbent member through the plunger.

BRIEF DESCRIPTION OF THE DRAWINGS

The above-mentioned and other features and advantages of this disclosure, and the manner of attaining them, will become more apparent and the disclosure itself will be better understood by reference to the following description of non-limiting embodiments of the disclosure taken in conjunction with the accompanying drawings, wherein:

FIG. 6A is a side view of the insertion portion of an applicator in accordance with one non-limiting embodiment of the present disclosure;

FIG. 6B is a side view of the insertion portion of an applicator in accordance with one non-limiting embodiment of the present disclosure;

FIG. 6C is a side view of the insertion portion of an applicator in accordance with one non-limiting embodiment of the present disclosure;

FIG. 9 is a perspective view of a package in accordance with one non-limiting embodiment of the present disclosure.

DETAILED DESCRIPTION OF THE INVENTION

Figure 1:
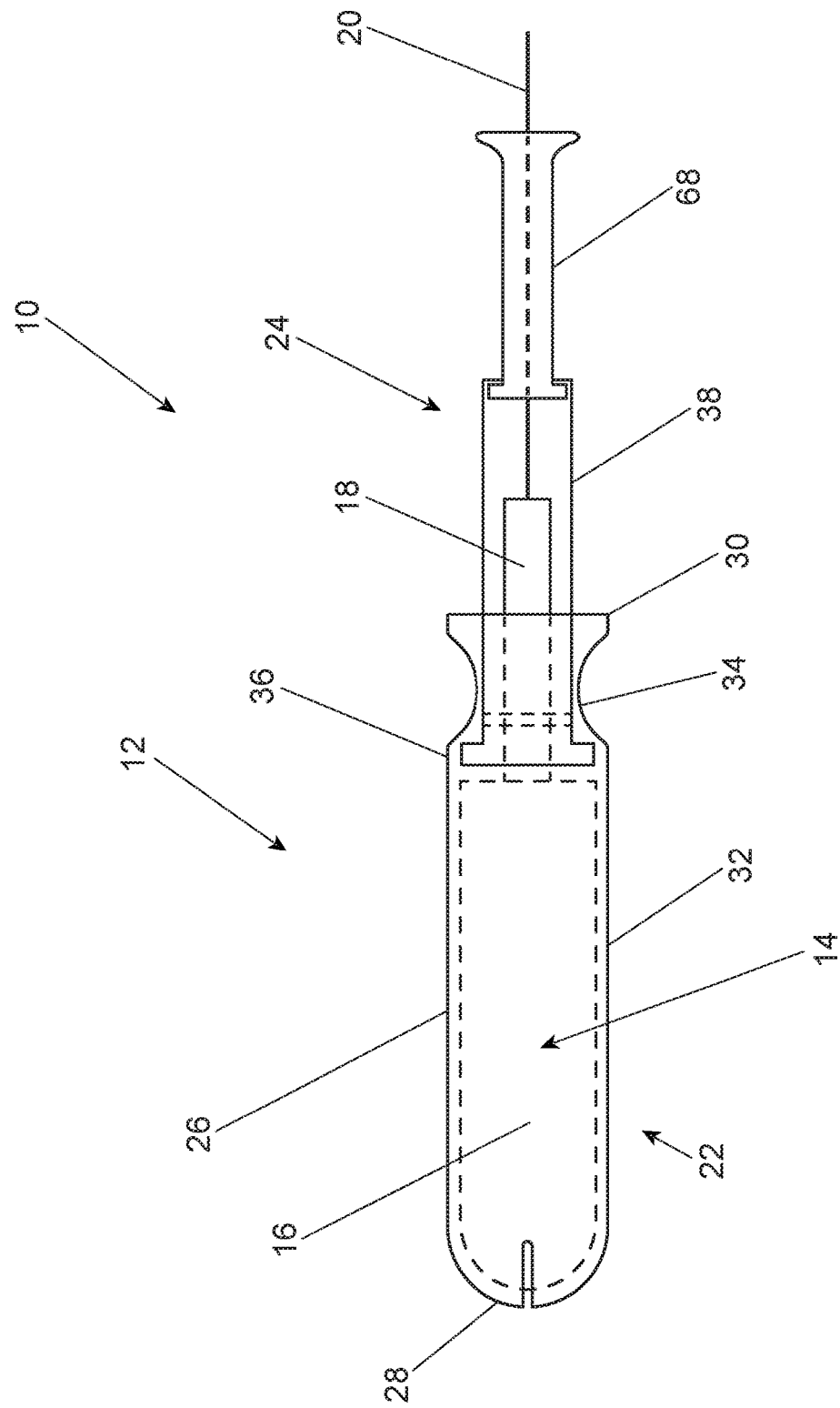
FIG. 1 is a side view of an applicator housing a tampon in accordance with one non-limiting embodiment of the present disclosure.

The present disclosure is directed to an improved feminine hygiene device having an indicator that communicates an improved perception of additional functional benefits, such as enhanced absorbency and/or leakage protection. Further, the improved feminine hygiene device provides an indication of proper configuration and insertion readiness.

As used herein, the term "feminine hygiene device" includes absorbent articles useful for feminine needs, such as articles that typically can be intended for feminine use internally, such as, for example, within a user's vagina. Internal feminine hygiene devices can include, for example, tampons and pessaries.

As used herein, the term "tampon" refers to any type of absorbent structure that can be inserted into the vaginal canal or other body cavity, such as, e.g., for the absorption of fluid, to aid in wound healing, and/or for the delivery of materials, such as moisture or active materials such as medicaments.

As used here, the terms "pledget" and "tampon pledget" are intended to be interchangeable and refer to a construction of absorbent material prior to compression of such construction into a tampon. A tampon pledget is sometimes referred to as a tampon blank, or a softwind, and the term "pledget" is intended to include such terms as well.

As used herein, the term "pessary" refers to any type of substantially non-absorbent structure for the purpose of reducing urine leakage and/or supporting a prolapsed uterus and/or bladder. Such pessaries can have any variety of shapes and sizes including cylinder, ovate, spherical, tubular, annular rings, "U" shaped, cup shaped, rings, cubes or donut shaped, and can function in any suitable manner, such as, e.g., by direct application of support, lever force, expansion of the device by selection of material, and/or by inflation of the device.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

As used herein, "applicator" refers to a device or implement that facilitates the insertion of a feminine hygiene device, such as, e.g., a tampon or pessary, into an external orifice of a mammal. Exemplary applicators include telescoping, insertion portion and plunger, and compact applicators.

As used herein, the term "insertion end" refers to the portion of the tampon or applicator including the end that is intended to enter the vaginal canal first when inserting the tampon or applicator into the vaginal canal.

As used herein, the term "withdrawal end" refers to the portion of the applicator opposite the insertion end and is intended to exit the vaginal canal first when the applicator is removed from the vagina.

As used herein, the term "barrel region" refers to the portion of the applicator adapted to house the feminine hygiene device. In certain embodiments, the barrel region includes the region of the applicator having the largest diameter.

As used herein, the term "indentation region" refers to the portion of the applicator adapted to provide a gripping surface that can facilitate grasping and/or holding of the applicator. In certain embodiments, the indentation region includes the region of the applicator having the smallest diameter.

As used herein, the term "shoulder region" refers to the upper region of the surface providing the slope or angle from the barrel region to the indentation region.

As used herein, the term "gripping formations" refers to raised or depressed structures provided at the indentation region of the applicator to assist a user in grasping the applicator. Suitable gripping formations include, e.g., projections, rings, ridges, ribs, embossments, and/or other raised surfaces.

As used herein, the term "color" includes any color, such as, for example, white, black, red, orange, yellow, green, blue, purple, brown, and/or any other color or declinations thereof.

As used herein, the term "same color" means colors having the same hue but which can differ in intensity, such as lightness and darkness.

As used herein, the term "visually perceptible" to a consumer is meant that a human viewer can visually discern a difference with the unaided eye (excepting standard corrective lenses adapted to compensate for nearsightedness, farsightedness, or astigmatism, or other corrected vision) in lighting at least equal to the illumination of a standard 100 watt incandescent white light bulb at a distance of 0.25 meter.

As used herein, the term "transparent" means that a consumer can visually perceive what is on the opposite side of the transparent object or thing. The term transparent also includes translucent regions.

As used herein, the term "opaque" means that a consumer cannot visually perceive what is on the opposite side of the opaque object or thing.

FIG. 1 illustrates one example embodiment of a hygiene device 10 comprising an applicator 12 housing a tampon 14.

The tampon 14 can comprise a primary absorbent member 16, a secondary absorbent member 18, and a withdrawal member 20. The applicator 12, which can house a tampon 14, can comprise an insertion portion 22 and a plunger 24. The insertion portion 22 comprises an outer surface 26 that defines an insertion end 28 and a withdrawal end 30, opposite the insertion end 28. The insertion portion 22 can also comprise a barrel region 32 intermediate the insertion end 28 and the withdrawal end 30. The barrel region 32 can be adapted to contain an absorbent product, such as a tampon 14.

As previously stated, the applicator 12 can also comprise a plunger 24. The plunger 24 can be operatively engaged with the insertion portion 22. Operatively engaged refers to the insertion portion 22 and the plunger 24 being configured for their intended purpose of housing and expelling a tampon 14 as is well known in the art. At least one of the insertion portion 22 and the plunger 24 can comprise a transparent region 38 and/or an opaque region 68. Both the transparent region 38 and the opaque region 68 can be a color, also referred to as an applicator color. The transparent region 38 allows a consumer to perceive the secondary absorbent member 18. This provides an advantage to the manufacturer of the tampon 14 because for the first time, the manufacturer can provide an applicator by which a consumer can truly appreciate the extra protection provided by the secondary absorbent member 18 of the tampon 14. Previous applicator designs left consumers largely unaware of the features of the secondary absorbent member 18. Now, consumers can perceive the technical features of the secondary absorbent member 18, such as, for example the length, thickness, and quality. Further, the opaque region 68 can provide a sense of discreetness, which consumers also desire in feminine hygiene devices, by covering the tampon so that it is not immediately identifiable. The following disclosure describes in more detail various embodiments of the hygiene device 10.

Figure 2:
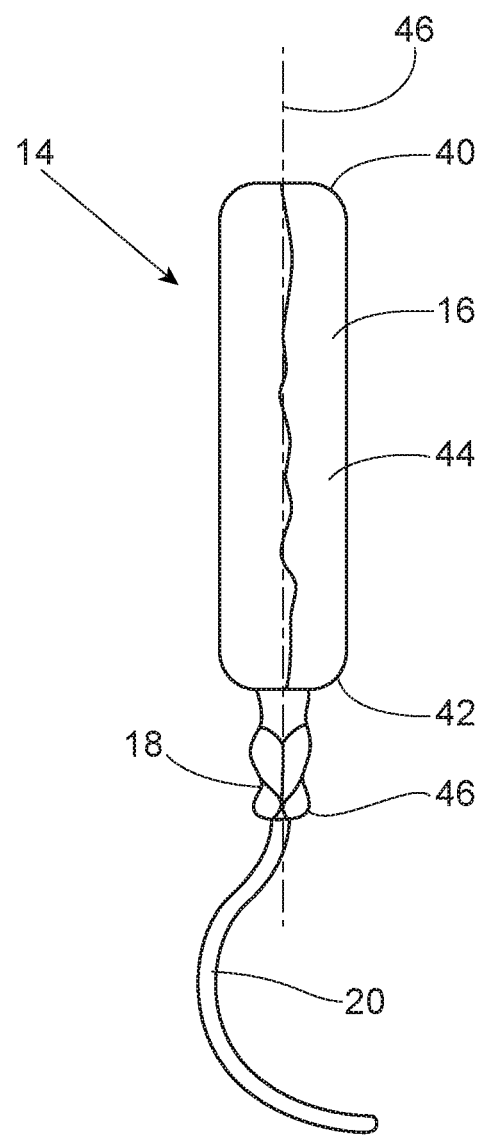
FIG. 2 is a side view of a tampon in accordance with one non-limiting embodiment of the present disclosure.

Referring to FIG. 2, as stated above, the tampon 14 can comprise a primary absorbent member 16, a secondary absorbent member 18, and a withdrawal member 20. The primary absorbent member 16 can comprise a leading end 40 and a trailing end 42, opposite the leading end 40. The primary absorbent member can also comprise an intermediate region 44 between the trailing end 42 and the leading end 40. The primary absorbent member 16 can be formed from a pledget (not shown). The pledget can be compressed into a tampon that can be, for example, a generally cylindrical configuration, as shown in FIG. 2. However, the primary absorbent member 16 can be compressed into other shapes including, for example, a rectangular shape or a semi-circular shape. The primary absorbent member can have a cross sectional shape such as a circle, rectangular, triangular, semi-circular, and other shapes that would allow for use as a tampon.

The primary absorbent member 16 can be constructed of a variety of fluid-absorbing materials, such as rayon, cotton, or comminuted wood pulp, which can be referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combination of material. Commonly used absorbent materials include cotton, rayon (including tri-lobal and conventional rayon fibers, and needle punches rayon), folded tissue, woven materials, nonwoven webs, synthetic and/or natural fibers. Additionally, superabsorbent materials can be incorporated into the tampon 14. The fluid absorbing materials allow the primary absorbent member 16 to have absorbency characteristics, which are referred to as a first absorbency.

Still referring to FIG. 2, the primary absorbent member 16 can be adjacent to and/or joined to at least one of a secondary absorbent member 18 and a withdrawal member 20. In another embodiment, the tampon 14 can comprise a primary absorbent member 16 and a secondary absorbent member 18. In yet another example embodiment, the tampon 14 can comprise a primary absorbent member 16 and a withdrawal member 20.

More specifically, in one example embodiment, the secondary absorbent member 18 can be disposed within a portion of the intermediate region 44 of the primary absorbent member 16 (not shown) and extend beyond the trailing end 42 of the primary absorbent member 16. Alternatively, in another example embodiment, the secondary absorbent member 18 can extend from the trailing end 42 of the primary absorbent member 16. The secondary absorbent member 18 can be joined to the primary absorbent member 16 mechanically and/or chemically. For example, the secondary absorbent member 18 can be mechanically tied, such as by being knotted, stitched/sewn, or woven, such as by a braid, to the primary absorbent member 16. The secondary absorbent member 18 can also be chemically bonded to the primary absorbent member 16 by glue or other adhesives suitable for use in hygiene devices.

The secondary absorbent member 18 can vary in shape. In one embodiment, the secondary absorbent member 18 can be generally cylindrical in shape, as shown in FIG. 2. In alternative embodiments, the secondary absorbent member 18 can be planar, rectangular, skirt-like, and/or semi-spherical. The secondary absorbent member 18 can be constructed of absorbent material. The absorbent material used to form the secondary absorbent member 18 can be uncompressed; or, if compressed, the absorbent material used to form the secondary absorbent member 18 can be compressed less than the absorbent material used to form the primary absorbent member 16. The absorbent material suitable for use in the primary absorbent member 16 can also be used as the absorbent material in the secondary absorbent member 18. Similar to the above, the absorbent materials allow for the secondary absorbent member 18 to have absorbency characteristics, which are referred to as a second absorbency. The first absorbency of the primary absorbent member 16 can be greater than the second absorbency of the secondary absorbent member 18.

The secondary absorbent member 18 can be designed to provide absorption in the lower vagina, also referred to as the portion of the vagina near the introitus. Thus, the secondary absorbent member 18 can be shaped such that the entire secondary absorbent member 18 can be located inside the vagina. Alternatively, a portion of the secondary absorbent member 18, depending on placement of the tampon 14 and the design of the secondary absorbent member 18, can be located outside the vagina. Further, the secondary absorbent member 18 can be designed such that it is comfortable for the consumer to wear and provides increased protection without requiring a change to the consumer's regular use habits.

Both the primary absorbent member 16 and the secondary absorbent member 18 can also comprise a first tampon color and a second tampon color, respectively. At least a portion of the second tampon color of the second absorbent member 18, prior to use, can be seen through the transparent region 38 of applicator 12 and/or plunger 24. Generally, any color can be used that allows consumers to identify the secondary absorbent member 18 as something different from the primary absorbent member 16 and/or the withdrawal member 20. For example, the secondary absorbent member 18 can be one or some combination of colors. In one example embodiment, the secondary absorbent member 18 can comprise a second tampon color being blue and the primary absorbent member 16 can comprise a first tampon color being white. Due to the difference in the first color and the second color, a consumer could immediately recognize that the primary absorbent member 16 is different from the secondary absorbent member 18. Thus, the first tampon color can be the same as or different from the second tampon color. More specifically, the first tampon color and the second tampon color can both be blue but have different intensity levels. Alternatively, the first tampon color can be pink and the second tampon color can be blue. Further, the difference in the first tampon color of the primary absorbent member 16 and the second tampon color of the secondary absorbent member 18 can signal to a consumer that the two members perform different functions during use of the tampon 14. For example, the difference in color can signal to a consumer that the primary absorbent member 16 has a first absorbency and the secondary absorbent member 18 has a second absorbency, which is different from the first absorbency. In another example, the difference in the first tampon color and the second tampon color can signal that the primary absorbent member 16 provides primary protection in one area of the vagina while the secondary absorbent member 18 provides subsequent leakage protection in another area of the vagina.

Still referring to FIG. 2, the tampon 14 can also comprise a withdrawal member 20. In one embodiment, as shown, the withdrawal member 20 can extend from the secondary absorbent member 18. In another embodiment, the withdrawal member 20 can extend from the primary absorbent member 16. The withdrawal member 20 can be used to withdraw the tampon 14 post use, to aid during insertion of the tampon 14, and/or to offer reassurance of proper placement post insertion of the tampon 14. More specifically, for example, the withdrawal member 14 can be used by the consumer to signal that the tampon 14 has been properly loaded in the applicator 12 by extending beyond the end of the applicator 12, which will be discussed in more detail below. Further, the withdrawal member 20 can signal proper placement post insertion by remaining external of the vagina.

The withdrawal member 20 can be disposed on at least one of the primary absorbent member 16 and the secondary absorbent member 18. Stated another way, the withdrawal member 20 can be integral with or an extension of another part of the tampon 14, such as the primary absorbent member 16 or the secondary absorbent member 18. More specifically, the withdrawal member 20 can be attached, mechanically and/or chemically, to the primary absorbent member 16 and/or the secondary absorbent member 18. The withdrawal member 20 should be attached such that the tampon 14 can withstand use and post use removal. In one example embodiment, the withdrawal member 20 can be sewn to the primary absorbent member 16. In another example embodiment, the withdrawal member 20 can be interweaved, such as by braiding, with the secondary absorbent member 18. Additionally, the withdrawal member 20 can be disposed on the primary absorbent member 16 and/or the secondary absorbent member 18 such that the withdrawal member 20 can extend in a direction substantially parallel to longitudinal tampon axis 46. Further, the withdrawal member 20 can be attached such that a portion of the withdrawal member 20 is surrounded axially by at least one of the primary absorbent member 16 and the secondary absorbent member 18. The withdrawal member 20 can be in a number of configurations such as a loop, a tab, or a string, which can be twisted or braided.

The withdrawal member 20 can be made from various materials to provide varying absorbency characteristics. In one embodiment, the withdrawal member 20 can be made hydrophobic to decrease or eliminate any absorbency characteristics. In another embodiment, the withdrawal member 20 can be made of absorbent materials, such as rayon and cotton. A withdrawal member 20 made from an absorbent material can have absorbency characteristics referred to as a third absorbency. In yet another embodiment, the withdrawal member 20 can be made to have both absorbent and non-absorbent characteristics. For example, the withdrawal member 20 can be made such that the portion of the withdraw member closest to the trailing end 42 of the primary absorbent member 16 can be absorbent and the portion of the withdrawal member 20 farthest from the trailing end 42 of the primary absorbent member 16 can be hydrophobic, also referred to as non-absorbent.

The withdrawal member 20 can also comprise a third tampon color. In one embodiment, the third tampon color can be different from the second tampon color of the secondary absorbent member 18 and/or the first tampon color of the primary absorbent member 16. In another embodiment, the third tampon color can be the same as the first tampon color of the primary absorbent member 16 and different from the second tampon color of the secondary absorbent member 18. As stated above, any color can be used that allows consumers to visually perceive that the secondary absorbent member 18 is something different from at least one of the primary absorbent member 16 or the withdrawal member 20.

In one example embodiment, the secondary absorbent member 18 can comprise a second tampon color being blue and the withdrawal member 16 can comprise a third tampon color being white. Due to the difference in color, a consumer would immediately recognize that the withdrawal member 20 is different from the secondary absorbent member 18. Further, the difference in color of the withdrawal member 20 and the secondary absorbent member 18 can signal to a consumer that the two members perform different functions during use of the tampon. More specifically, a consumer can identify that the secondary absorbent member 18 provides some leakage protection and has some level of absorbency while the withdrawal member 20 provides minimal leakage protection and has a lower level of absorbency than the secondary absorbent member 18. Further, when the consumer goes to remove the tampon 14 post use, the consumer can readily differentiate between the withdrawal member 20 including a third tampon color and the secondary absorbent member 18 including a second tampon color, which is different than the third tampon color. This is an advantage to manufacturers because it offers consumers assurance that their product is going to provide the optimum protection and guidance on proper use of the product.

Figure 3:
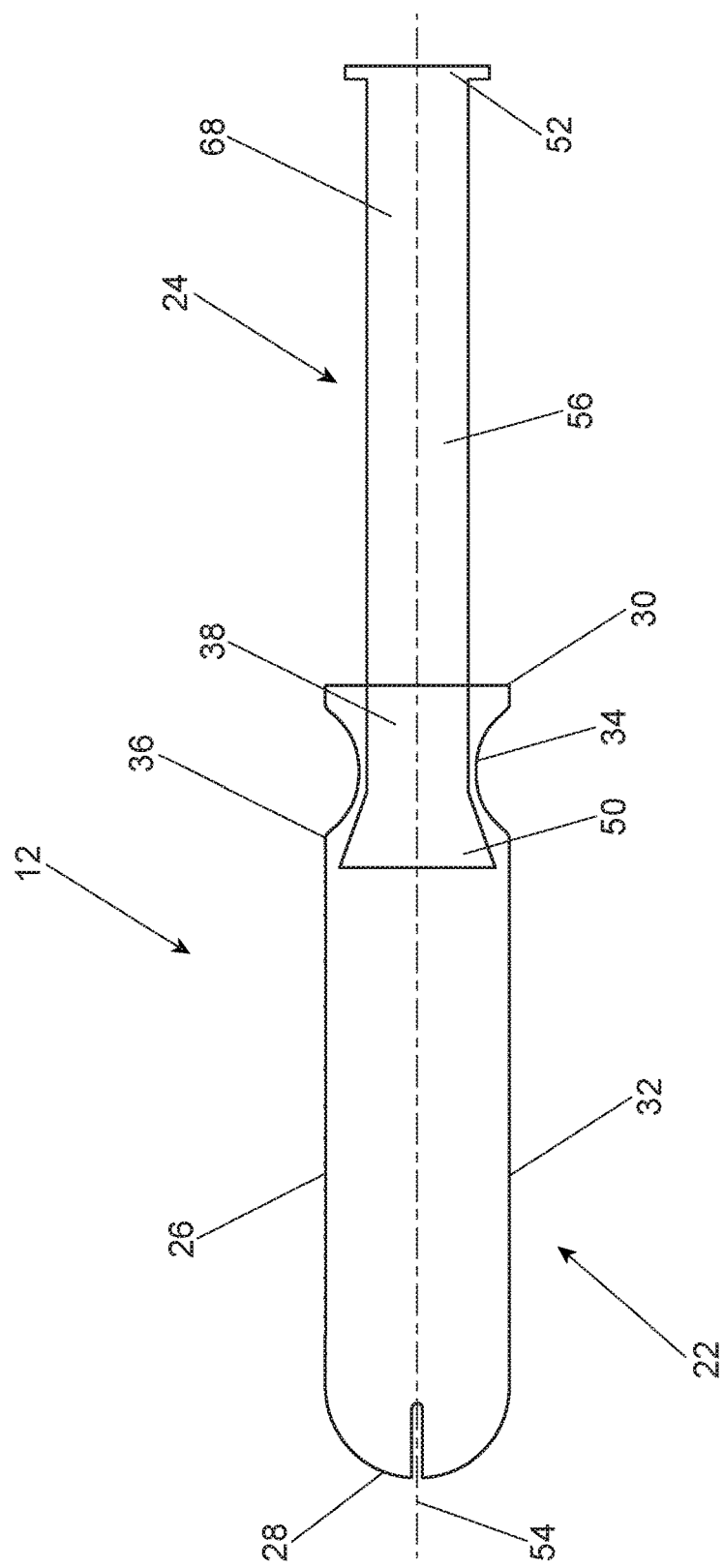
FIG. 3 is a side view of an applicator in accordance with one non-limiting embodiment of the present disclosure.
Figure 4:
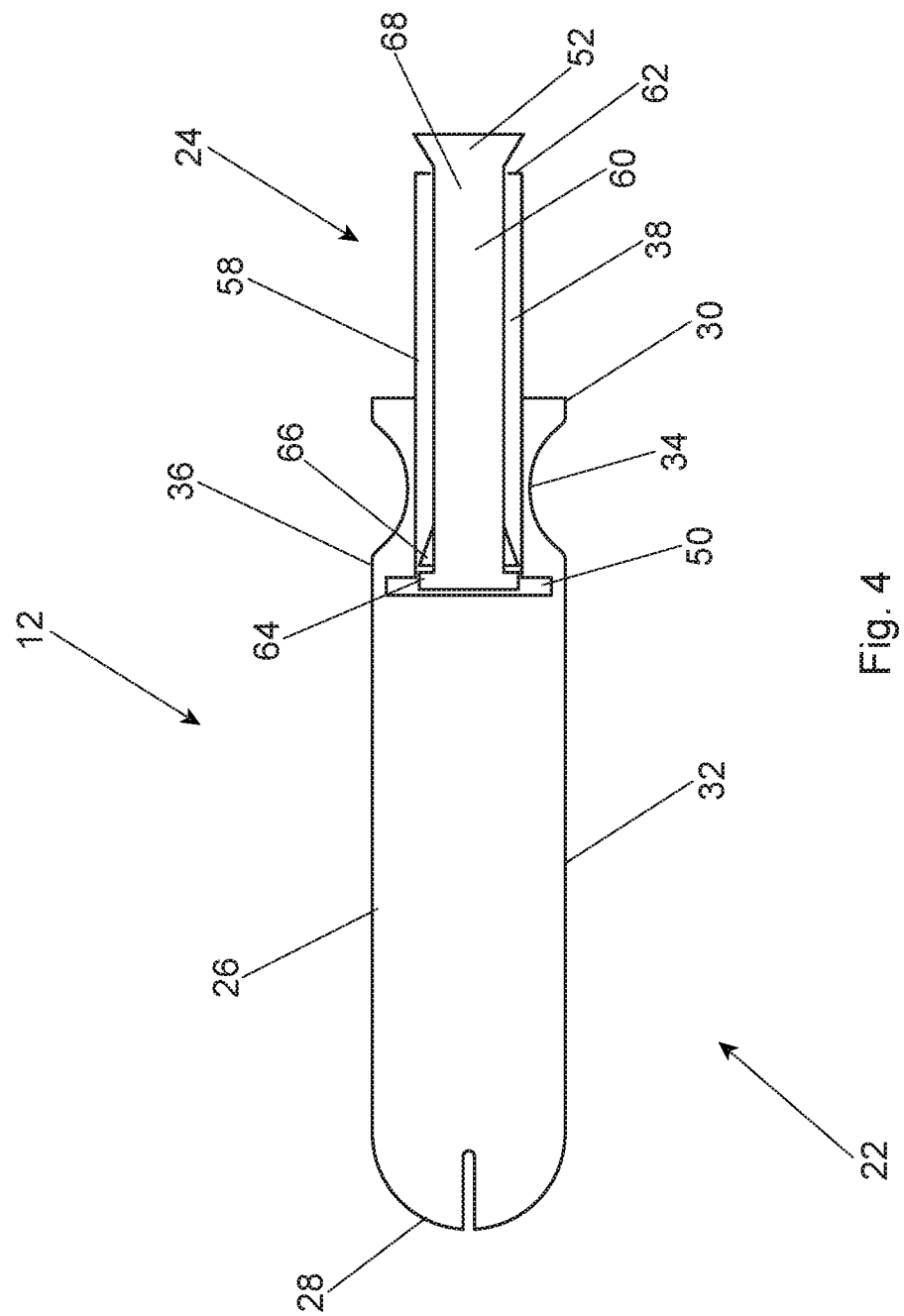
FIG. 4 is a side view of an applicator in accordance with one non-limiting embodiment of the present disclosure.
Figure 5:
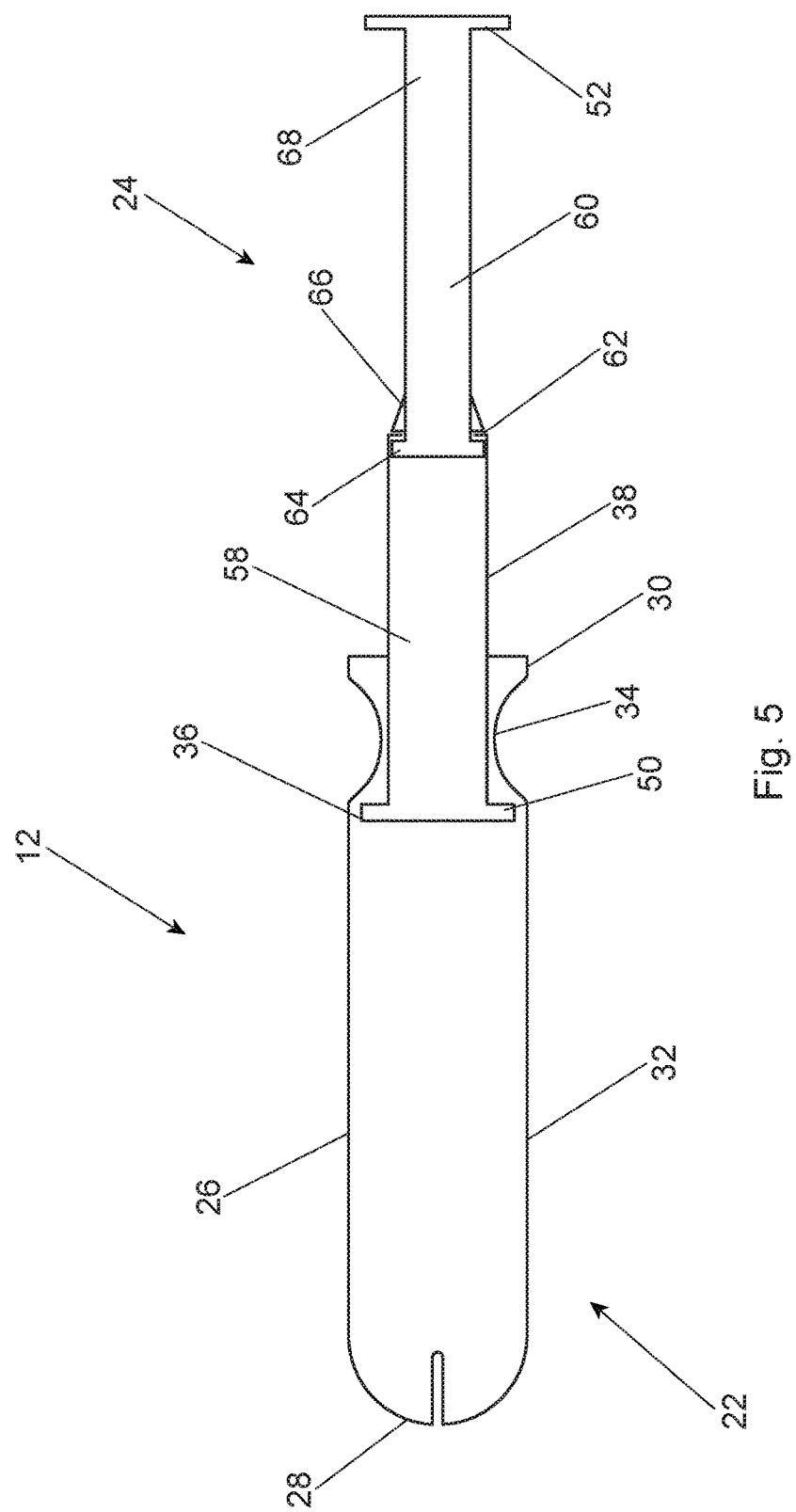
FIG. 5 is a side view of an applicator in accordance with one non-limiting embodiment of the present disclosure.

As previously stated, an applicator 12 can house the tampon 14. FIGS. 3, 4, and 5 illustrate an applicator 12. The applicator 12 can comprise an insertion portion 22 and a plunger 24. The insertion portion 22 comprises an outer surface 26 that defines an insertion end 28 and a withdrawal end 30, opposite the insertion end 28. The insertion portion 22 can also comprise a barrel region 32 intermediate the insertion end 28 and the withdrawal end 30. The barrel region 32 can be adapted to contain an absorbent product, such as a tampon 14.

In one example embodiment, the insertion portion 22 can also comprise an indentation region 34. The indentation region 34 can extend inwardly from the outer surface 26 and can be disposed between the barrel region 32 and the withdrawal end 30. Stated another way, the indentation region 34 protrudes inward from the outer surface 26 of the insertion portion 22. The indentation region 34 can be disposed circumferentially around the outer surface 26 of the insertion portion 22. In addition, the indentation region 34 can be adjacent to a shoulder region 36. The shoulder region 36 can be disposed between the barrel region 32 and the indentation region 34. Generally, the shoulder region 36 refers to the area of the insertion portion 22 that slopes from the barrel region 32 to the indentation region 34. The indentation region 34 can be any shape that allows the consumer to grip the applicator 12. More specifically, for example, the indentation region 34 can be a concave shape or a square shape or some other shape having at least one of curved and straight portions.

In one embodiment, the indentation region 34 can comprise gripping formations 48, as shown in FIGS. 6A-6C. The gripping formations 48 can protrude from the outer surface 26 and extend from the indentation region 34 to the shoulder region 36 and/or the barrel region 32. The gripping formations 48 can be provided in any suitable shape, such as, for example, longitudinal formations, waves, swirls, or a substantially contiguous pattern of joined elements. The gripping formations 48 can comprise projections, rings, ridges, ribs, embossments, depressions, grooves, and/or other gripping structures. The gripping formations 48 can be provided in any suitable manner, such as, by the addition of material, and/or by impressing, such as, by embossing, or compressing the surfaces.

Further, the indentation region 34 can comprise any suitable shape that can facilitate grasping and/or holding of the applicator 12. For example, the indentation region 34 can be a shape suitable for positioning one or more of the consumer's fingers within the indentation region 34. In another example, the indentation region 34 can have a shape such that the cross-section can be, for example, circular, oval, elliptical, square, rectangular, triangular, polygonal, or some other shape having one or more curved and/or one or more straight sides. Additional features of the indention region and gripping formations can be found in U.S. Pat. No. 8,449,491.

The insertion portion 22 can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, poly lactic acid, poly hydroxyalkanoate, ethylene vinyl acetate, polyurethane, silicone, derivatives thereof, copolymers thereof, mixtures thereof, or any suitable smooth plastic material. Examples of suitable materials are disclosed in U.S. Pat. Nos. 5,346,468 and 5,558,631. In certain embodiments, additives can be included in the material to alter or enhance certain material properties. Suitable additives include, for example, mold release agents, slip agents, surface energy modifiers, pearlescent agents, and/or any other suitable additives. In certain embodiments, the insertion portion can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the insertion portion 22 can include a textured surface. Texture can be provided in any suitable manner, such as, e.g., by designing texture into or adding texture to the insertion portion.

Further to the above, the insertion portion 22 can comprise an applicator color. More specifically, the applicator color can cover a portion or all of the outer surface 26 of the insertion portion 22. For example, in one embodiment, the insertion portion 22 can comprise an applicator color being blue. In another example embodiment, the insertion portion 22 can comprise two or more colors, such as, for example, a first applicator color and a second applicator color. More specifically, the barrel region 32 can comprise a first applicator color and the indentation region 34 and/or the shoulder region 36 can comprise a second applicator color, different from the first applicator color. For example, a barrel region 32 can comprise a first applicator color being light blue that is not different from an indentation region 34 comprising a second applicator color being dark blue color; whereas, a barrel region 32 comprising a first applicator color being purple is different from an indentation region 34 comprising a second applicator color being blue.

However, despite the colors being the same, the consumer can still perceive the colors as being different. Thus, the consumer could have a first visual impression when he or she views the first applicator color being light blue and a second visual impression when he or she views the second applicator color being dark blue. In addition, a consumer who has a first visual impression and a second visual impression could still find that the applicator and tampon are cohesive with one another or belong together. For example, still referring to the above description, the first applicator color and the second applicator are different hues of blue and, as such, can be identified to belong together or, stated another way, to be cohesive.

In yet another example embodiment, an insertion portion 22 can comprise a transparent region 38 and/or an opaque region 68. Generally, a transparent region 38 allows the consumer to perceive that which is housed within the applicator 12 and, thus, to have one or more visual impressions. Further, an opaque region 68 does not allow the consumer to perceive that which is housed within the applicator 12. For example, the barrel region 32 can be a transparent region 38 and the indentation region 34 can be an opaque region 68. Both the transparent region 38 and the opaque region 68 can comprise one or more colors. Alternatively, the transparent region 38 can be clear, such that the transparent region 38 displays without distortion, such as a color change, that which is housed within the insertion portion 22. In yet another embodiment, the transparent region 38 can be clear but can provide some other enhanced feature, such as amplification and/or color change, such that the transparent region 38 displays with some distortion that which is housed within the applicator 12.

For example, in one embodiment, a hygiene device 10 can comprise a tampon 14 being housed within an applicator 12 comprising a barrel region 32 comprising an opaque region 68 and an indentation region 34 comprising transparent region 38. A consumer using such product could visually perceive, such as by a visual impression, the tampon 14 through the transparent region 38 of the applicator 12 but would not be able to visually perceive the tampon 14 through any opaque region 68 of the applicator 12. This is an advantage to both consumers and manufacturers. Manufacturers are able to add distinguishing technical features, such as texture, color, indicia, and the like to their products to signal to consumers that the products contain these features. More specifically, consumers can now perceive features such as the secondary absorbent member 18 through the applicator 12, and better understand the improved function, such as absorbency, of the tampon 14. Consumer's understanding of a product's advanced technical features will often result in improved sales for manufacturers and improved consumer satisfaction due to being informed of a product's technical advantages, ease of use, and superior performance.

Still referring to FIGS. 3, 4, and 5, as previously stated, the applicator 12 can also comprise a plunger 24 operatively engaged with the insertion portion 22. The plunger 24 and insertion portion 22 are configured with respect to one another such that the plunger 24 can expel the tampon 14 form the insertion portion 22 of the applicator 12. The plunger 24 can be a single, elongated member as shown in FIG. 3, or the plunger 24 can be a multi-component, elongated member as shown in FIGS. 4 and 5.

The single, elongated plunger 24, as shown in FIG. 3, can comprise a deployment end 50, a stopper 52, opposite the deployment end 50, and an elongated body 56 disposed between the deployment end 50 and the stopper 52. The deployment end 50 can engage the tampon 14 housed within the insertion portion 22 such that when a consumer exerts an axial force against the stopper 52 or the elongated body 56 in a direction substantially parallel to the longitudinal applicator axis 54, the tampon 14 can be driven through the barrel region 32 and expelled out the insertion end 28 of the insertion portion 22. The deployment end 50 can be any shape that would allow the tampon 14 to be engaged and driven through the insertion portion 22, and that would allow the secondary absorbent member 18 and/or the withdrawal member 20 to be appropriately housed in the applicator 12. For example, as shown in FIG. 3, the deployment end 50 is a conical shape that would allow for the trailing end 42 of the tampon 14 (not shown) to be properly engaged and for the other parts of the tampon 14, such as the withdrawal member 20, to be housed in the applicator. In an alternative embodiment, the deployment end 50 can be a substantially flat shape, as shown in FIG. 4. Further to the above, the deployment end 50 can keep the plunger 24 from being removed from the insertion portion 22 through the withdrawal end 30. The deployment end 50 can be sized such that it is held in place by the shoulder region 36 and/or the indentation region 34. Thus, the plunger 24 can aid the consumer in ensuring that the applicator 12 is in proper configuration for use.

The plunger can also comprise a stopper 52. The stopper 52 can provide a place for the consumer to exert a force on the applicator 12 to deploy the tampon 14 for insertion. Further, the stopper 52 can engage the withdrawal end 30 of the insertion portion 22 post insertion of the tampon 14 to signal to the consumer that the tampon 14 has been fully deployed and/or to keep the plunger 24 from fully entering the insertion portion 22. Thus, the stopper 52 can have a diameter and/or a length longer than or equal to the diameter and/or length of the withdrawal end 30. The stopper 52 can be any shape that allows the consumer an area to place their fingers and to exert a force on the plunger 24, and the stopper can be wide enough such that the plunger 24 cannot fully enter the insertion portion 22. Further, the stopper 52 can allow for the withdrawal member 20 of the tampon 14 to protrude through the end of the plunger 24. This allows the consumer to be sure that the tampon 14 is properly loaded in the applicator 12 and is ready for use.

The plunger 24, as shown in FIG. 3, can comprise a transparent region 38 and/or an opaque region 68. Both of the transparent region 38 and the opaque region 68 can comprise a color, also referred to as an applicator color. The transparent region 38 of the plunger 24 can allow the consumer to observe the tampon 14 in the applicator 12 pre-use. This can allow the consumer to formulate a visual impression of the tampon 14. For example, in one embodiment, the plunger 24 can comprise a transparent region 38 such that a consumer can perceive the secondary absorbent member 18 of the tampon 14 through the plunger 24. For example, the secondary absorbent member 18 can comprise a second tampon color being blue and the plunger 24 can comprise a transparent region 38 including a third applicator color being yellow. Thus, the consumer can perceive a secondary absorbent member 14 housed within the plunger 24 that appears to be green. In yet another example, the secondary absorbent member 14 can comprise a second tampon color being purple and the plunger 24 can comprise a transparent region 38 that is clear. Thus, the consumer can perceive a secondary absorbent member 14 that comprises a second tampon color that is purple through the plunger 24. By contrast, those portions of the tampon 14 housed within the opaque region 68 of the plunger 24 cannot be visually perceived by the consumer.

Further to the above, the transparent region 38 can be sized such that at least one of the primary absorbent member 16, the secondary absorbent member 18, and the withdrawal member 20 can be viewed through the applicator 12. For example, the plunger 24 can comprise a transparent region 38 such that a portion of the secondary absorbent member 18 and a portion of the withdrawal member 20 can be perceived through the plunger 24 prior to insertion (as shown in FIG. 1, for example). More specifically, the secondary absorbent member 18 can comprise a second tampon color such as pink and the withdrawal member can comprise a third tampon color such as white. A consumer viewing the tampon 14 having the above mentioned colors through the transparent region 38 of the applicator 12 could perceive that the secondary absorbent member 18 as being pink and the withdrawal member 20 as being white. The variation in color of the different members of the tampon 14 provides a functional signal to the consumer. It allows the consumer to understand that the secondary absorbent member 18 is different from the withdrawal member 20 and further highlights the added functionality, such as increased protection, provided by the secondary member 18. Additionally, it provides an indication to the consumer that the secondary absorbent member 18 is adequately attached to the withdrawal member 20, which is assurance to the consumer that the tampon is going to act appropriately during use and removal.

In another example embodiment, the plunger 24 can comprise a transparent region 38 such that a portion of the secondary absorbent member 18 and a portion of the withdrawal member 20 can be perceived through the plunger 24 prior to insertion (as shown in FIG. 1, for example). More specifically, the secondary absorbent member 18 can comprise a second tampon color such as blue and the withdrawal member can comprise a third tampon color such as white. Further, the transparent region 38 can be a color such as red. Thus, a consumer viewing the tampon 14 having the above mentioned colors through the transparent region 38 of the applicator 12 could perceive that the secondary absorbent member 18 as being purple and the withdrawal member 20 as being red. Further, the consumer can view the portion of the withdrawal member 20 being outside the applicator 12 as being white. Accordingly, the consumer then can be said to have a first visual impression of the secondary member as being purple, a second visual impression of the withdrawal member as being red and a third visual impression of the withdrawal member being white.

The plunger 24 can comprise one or more colors. More specifically, the plunger 24 can comprise a fourth applicator color and a fifth applicator color. Thus, in one example embodiment, the plunger 24 can comprise a stopper 52, a deployment end 50 opposite the stopper 52, and an elongated body 56 intermediate the stopper 52 and the deployment end 50. The stopper 52 can comprise a fourth applicator color being blue and the elongated body 56 can comprise a fifth applicator color being light blue. The visual perception of the change in color could lead a consumer to believe that the stopper 52 does something different than the elongated body 56. More specifically, the stopper 52 having a different color can communicate to the consumer that some interaction may be required with that portion of the applicator. These visual cues can result in the consumer's ease of use of the product.

Referring to FIGS. 4 and 5, the plunger 24 can be a multi-component plunger 24, referred to as a compact applicator when in combination with an insertion portion 22. A multi-component plunger 24 is one in which multiple components need to be assembled to produce a rigid, elongated member sufficient to engage and expel a tampon 14 from an insertion portion 22. FIGS. 4 and 5 illustrate a multi-component plunger 24 having two parts: a first component 58 and a second component 60. The second component 60 can be slidably engaged with the first component 58. More specifically, the second component 60 can be designed such that it can be slid within the first component 58 or around the first component 58 (not shown).

In one example embodiment, as disclosed above, the plunger 24 can comprise a deployment end 50. The deployment end 50 can be disposed on the first component 58. The first component can further comprise a lip 62. The lip 62 can engage with a ridge 64 of the second component 60. The second component 60 can also comprise a projection 66 that can also engage the lip 62. The engagement of the lip 62 with the ridge 64 and the projection 66 allows the two components of the plunger 24 to be removably locked into a rigid, elongated configuration, as shown in FIG. 5. One of ordinary skill in the art would understand that a series of nested components slidably engaged with one another could be removably locked to one another to form a plunger 24 suitable for use in an applicator 12. Having a multi-component plunger 24 allows the hygiene device 10 to be reduced in size and, thus, to be sold in smaller packaging, which can result in a cost reduction for manufactures and increased discreetness for consumers.

The plunger 24 can comprise one or more colors. More specifically, the plunger 24 can comprise a fourth applicator color and a fifth applicator color. Thus, in one example embodiment, the plunger 24 can comprise a first component 58 and a second component 60 slidably engaged with the first component 58. The first component can comprise a fourth applicator color being orange and the second component 60 can comprise a fifth applicator color being pink. Any number of components that make up the rigid, elongated plunger 24 useful in expelling a tampon 14 from an applicator 12 can have any number of colors. Thus, the first component 58 can comprise one or more colors and the second component 60 can comprise one or more colors. The colors on each of the first component 58 and the second component 60 can be the same or different.

Similar to the above, the plunger 24 can comprise a transparent region 38 and/or an opaque region 68. Any component of a multi-component plunger 24 can comprise one or more transparent regions 38 and/or one or more opaque regions 68. In one example embodiment, as shown in FIGS. 4 and 5, the first component 58 can be a transparent region 38 and the second component 60 can be a transparent region 38. Thus, the tampon 14 can be perceived through the first component 58 of the plunger 24. Further, the transparent region 38 can comprise a color so long as the tampon 14 can still be visually perceived through the plunger 24. The second component 60 can also be a transparent region 38. The transparent region 38 of the second component 60 can be clear or a color, which can be the same as or different from the color of the transparent region 38 of the first component 58.

In another embodiment, the first component 58 can comprise a transparent region 38 and the second component can be an opaque region 68. An opaque region is a region in which the tampon 14 is not visible through the applicator 12. An opaque region 68 can have a color. For example, the first component 58 can be a transparent region 38 being clear and the second component 60 can comprise an opaque region 68 and a fourth applicator color being orange. The color of the opaque region 68 can be the same as any other region of the applicator. Further to the above, the first component 58 can comprise a transparent region 38 and/or an opaque region 68. Similarly, the second component region 60 can comprise a transparent region 38 and/or an opaque region 68. Each of the first component 58 and the second component 60 can comprise one or more colors.

Figure 7:
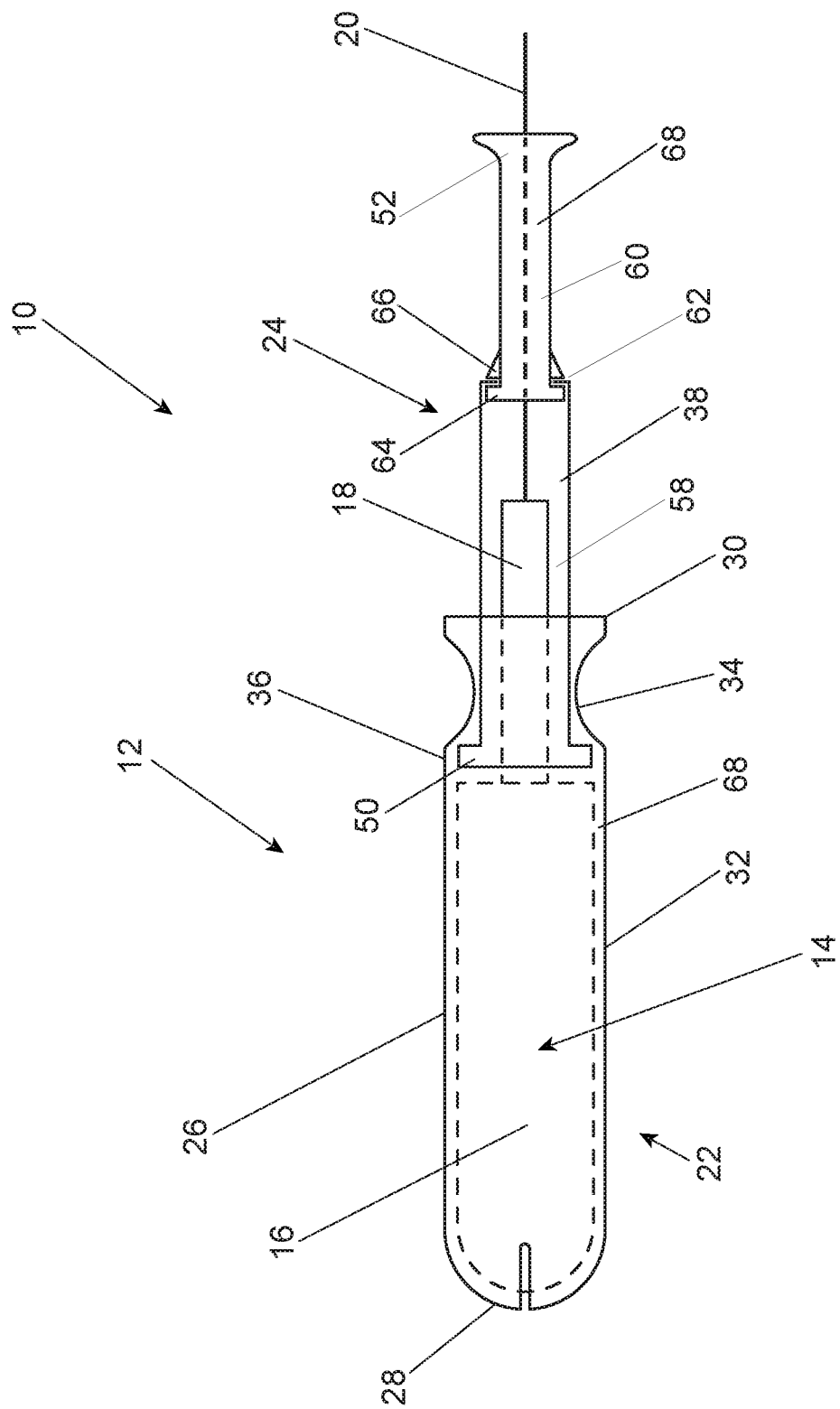
FIG. 7 is a side view of an applicator housing a tampon in accordance with one non-limiting embodiment of the present disclosure.

Example embodiments will be described herein with reference to FIGS. 7 and 8. Referring to FIG. 7, the hygiene device 10 comprises an applicator 12 housing a tampon 14. The tampon 14 can comprise a primary absorbent member 16, a withdrawal member 20 adjacent the primary absorbent member 16, and a secondary absorbent member 18 disposed intermediate the primary absorbent member 16 and the withdrawal member 20. The secondary absorbent member 18 can comprise a second tampon color such as blue. The primary absorbent member 16 and the withdrawal member 20 can each comprise a first tampon color and a third tampon color, respectively. The second tampon color and the third tampon color can be substantially the same color, such as, for example white. Thus, the second tampon color is different from both the first tampon color and the third tampon color. Further, the primary absorbent member 16 can comprise a first absorbency, the secondary absorbent member 18 can comprise a second absorbency, and the withdrawal member 20 can comprise a third absorbency. The first absorbency can be greater than both the second absorbency and the third absorbency, and the second absorbency can be greater than the third absorbency.

Still referring to FIG. 7, the applicator 12 can comprise an insertion portion 22 and a plunger 24. The insertion portion 22 can comprise an outer surface 26 defining a barrel region 32. The barrel region 32 surrounds the primary absorbent member 16. Further, the insertion portion 22 comprises an insertion end and a withdrawal end 30, opposite the insertion end 28, between which the primary absorbent member 16 can be located when housed within the insertion portion 22. The insertion portion 22 can comprise opaque regions 68 and/or transparent regions 38. In the example embodiment shown in FIG. 7, the insertion portion 22 comprises an opaque region 68 such that the primary absorbent member 16 is not visually perceptible through the outer surface 26. Still further, the insertion portion 22 can comprise one or more colors.

In one embodiment, the insertion portion 22 can comprise a first applicator color. The first applicator color can be the same or different from any one of the first tampon color, second tampon color, and third tampon color. In one example embodiment, the first applicator color can be the same as the second tampon color of the secondary absorbent member 18 and different from at least one of the first tampon color of the primary absorbent member 16 and the third tampon color of the withdrawal member 20. More specifically, the first applicator color of the insertion portion 22 can be blue and the second tampon color of the secondary absorbent member 18 can be blue and both the first tampon color and the third tampon color can be white. A consumer can identify two colors as being blue despite the colors having two different intensity levels. Thus, the two colors can be identified as the same color that have the same hue but differ in intensity, also referred to as lightness or darkness of the color. Those colors having the same hue but different intensity levels can be the same color for purposes of the present disclosure. For example, an insertion portion 22 comprising a first applicator color being dark pink and a secondary absorbent member 18 comprising a second tampon color being light pink can both be identified as being pink, which would be the same color, not different from one another.

The applicator 12 can also comprise a plunger 24 operatively engaged with the insertion portion 22. The plunger 24, as shown in FIG. 7, is a multi-component plunger 24 comprising a first component 58 and a second component 60. The first component 58 and the second component 60 engage to form a rigid, elongated member that can deploy a tampon 14. The first component 58 and the second component 60 house the secondary absorbent member 18 and at least a portion of the withdrawal member 20. The first component 58 can comprise a transparent region 38 such that at least a portion of the secondary absorbent member 18 can be visually perceived through the applicator 12. The first component 58 can be sized such that not only a portion of the secondary absorbent member 18 can be visually perceived but a portion of the withdrawal member 20 can also be visually perceived. This allows a consumer not only to appreciate the technical features of the secondary absorbent member such as absorbency and thickness, but also to compare the secondary absorbent member 18 with the withdrawal member 20. The consumer can see the difference in thickness, which can be interpreted as a difference in absorbency. Further, the consumer can become educated about the different functional roles of the secondary absorbent member 18 and the withdrawal member 20. A perceptible view of the withdrawal member 20 and its location to the secondary member 18 can aid in post use removal of the tampon. Upon the time of removal, the consumer knows that the withdrawal member 20 is located adjacent to the secondary absorbent member 18 and that the withdrawal member 20 is different from the secondary absorbent member 18. Thus, if the consumer locates the secondary absorbent member prior to the withdrawal member, the consumer will likely be able to quickly find the withdrawal member due to knowing its relationship to the secondary absorbent member prior to use. Further, having the ability to view both the secondary absorbent member and the withdrawal member offers reassurance that the tampon is configured properly, all parts are adequately connected, and that the tampon is ready for insertion by observing each part of the tampon elongated. Additionally, the withdrawal member 20 can extend from the end of the plunger 24 such that a portion remains external of the applicator 12. This also aids in the consumer's visual perception that the tampon is configured properly and the location of the withdrawal member 20 in relation to other members of the tampon 14.

As illustrated in FIG. 7, the second component 60 can comprise an opaque region 68. Thus, the withdrawal member 20 cannot be visually perceived through the second component 60. The second component 60 can comprise a second applicator color. The second applicator color can be the same as the second tampon color of the secondary absorbent member 18 and the first applicator color of the insertion portion 22. For example, in one embodiment, all of the second applicator color, first tampon color, and first applicator color can be orange, and the first tampon color of the primary absorbent member 16 and the third tampon color of the withdrawal member 20 can be a color other than orange. Further, the first component 58 can comprise a transparent region 38 that is clear. The configuration of this embodiment and similar embodiments gives consumers a signal that the hygiene device is ready for use. More specifically, a consumer of a hygiene device, as previously described, would be able to perceive the orange insertion portion 22 followed by the orange secondary absorbent member 18 followed by the orange second component 60 of the plunger 24. This use of color signals to the consumer that the tampon 14 is appropriately housed within the applicator 12 and is in a position to be inserted. The continuum of the same color is a signal to the consumer that the tampon is properly configured and ready for use.

Figure 8:
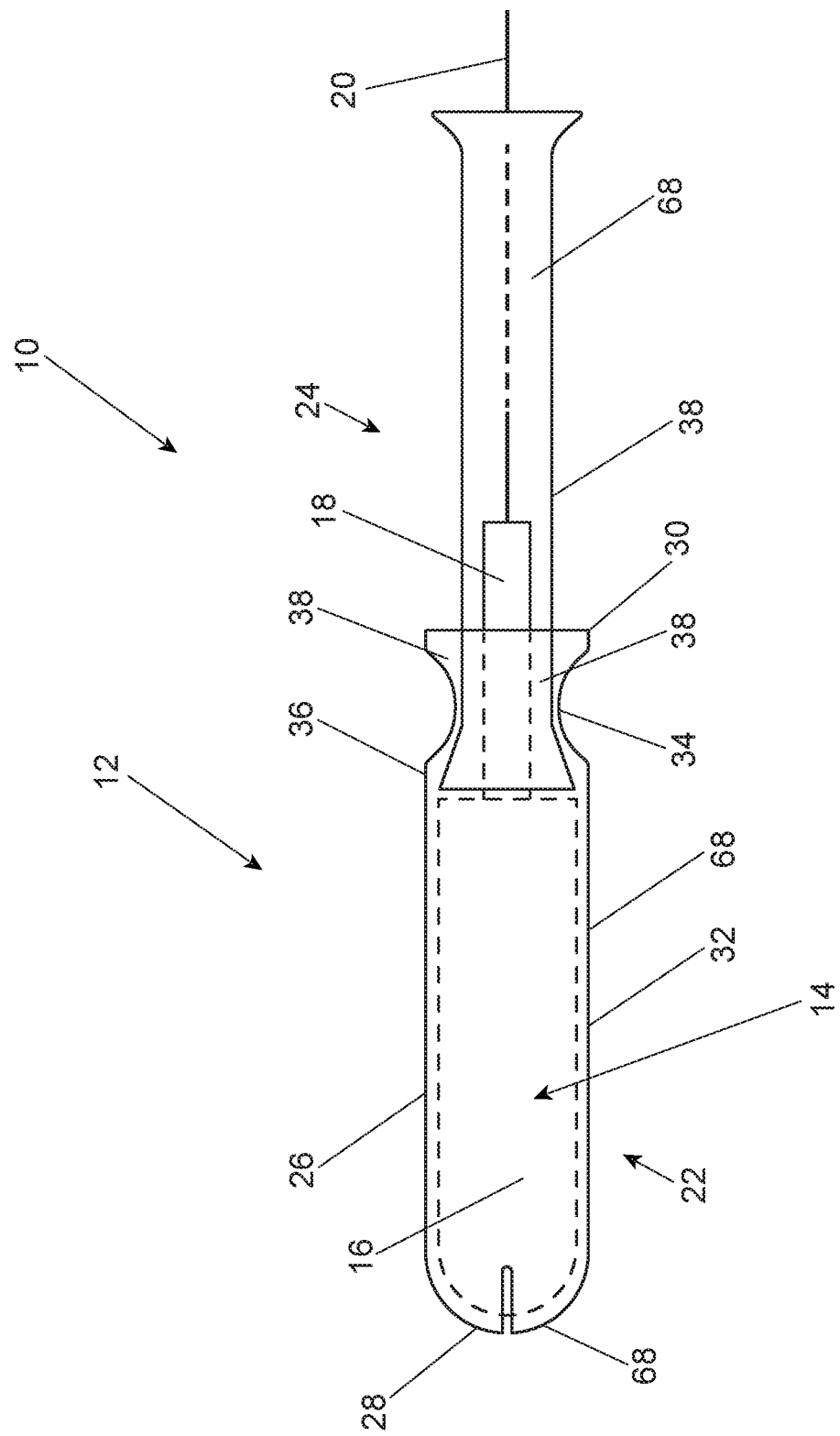
FIG. 8 is a side view of an applicator housing a tampon in accordance with one non-limiting embodiment of the present disclosure.

Referring now to FIG. 8, the applicator 12 can house a tampon 14. The tampon 14 as previously disclosed with respect to FIG. 7 can be used in the applicator as illustrated in FIG. 8. The applicator 12 can comprise an insertion portion 22 and a plunger 24. The insertion portion 22 can comprise an outer surface 26 defining a barrel region 32. The barrel region 32 surrounds the primary absorbent member 16. Further, the insertion portion 22 comprises an insertion end 28 and a withdrawal end 30, opposite the insertion end 28, between which the primary absorbent member 16 can be located when housed within the insertion portion 22. The insertion portion 22 can comprise an opaque region 68 and/or a transparent region 38. In the example embodiment shown in FIG. 8, the insertion portion 22 comprises an opaque region 68 and a transparent region 38. More specifically, the barrel region 32 and the insertion end 28 can comprise an opaque region 68 such that the primary absorbent member 16 is not visually perceptible through the outer surface 26. The shoulder region 36, indentation region 34, and withdrawal end 30 can comprise a transparent region 38 such that the tampon 14 can be visually perceived through these portions of the applicator 12.

Still further, the insertion portion 22 can comprise one or more colors. In one embodiment, the insertion portion 22 can comprise a first applicator color. The first applicator color can be the same or different from the first tampon color, second tampon color, and third tampon color. In one example embodiment, the first applicator color can be the same as the second tampon color of the secondary absorbent member 18 and different from at least one of the first tampon color of the primary absorbent member 16 and the third tampon color of the withdrawal member 20. More specifically, the first applicator color of the insertion portion 22 can be green, the second tampon color of the secondary absorbent member 18 can be green, and both the first tampon color and the third tampon color can be a color other than green. A consumer can identify two colors as being green despite the colors having two different intensity levels. Thus, two colors can be identified as the same color that have the same hue but differ in intensity levels, also referred to as lightness or darkness of the color. Stated differently, those colors having the same hue but different intensity levels can be the same color for purposes of the present disclosure. For example, an insertion portion 22 comprising a first applicator color being dark yellow and a secondary absorbent member 18 comprising a second tampon color being light yellow can both be identified as being yellow, which would be the same color for purposes of the present disclosure.

The applicator 12 can also comprise a plunger 24 operatively engaged with the insertion portion 22. The plunger 24 as shown in FIG. 8, is a single-component plunger 24 comprising a deployment end 50, a stopper 52 opposite the deployment end 50, and an elongated body 56 disposed between the deployment end 50 and the stopper 52. The plunger 24 can comprise a transparent region 38 and/or an opaque region 68. In one embodiment, as illustrated in FIG. 8, the deployment end 50 and a portion of the elongated body 56 proximal the indention region 34 can be a transparent region 38. Thus, the secondary absorbent member 18 can be visually perceived through the insertion portion 22 and this portion of the plunger 24. Further, the elongated body 56 distal the insertion portion 22 can comprise an opaque region 68, which does not allow the consumer to visually perceive the withdrawal member 20 and/or a portion of the secondary absorbent member 18 through the plunger 24. The size of both the transparent region 38 and the opaque region 68 along the length of the plunger can vary. Having at least a portion of the secondary absorbent member 18 visible through the insertion portion 22 and/or the plunger 24 allows a consumer to appreciate the technical features of the secondary absorbent member 18 such as the absorbency and thickness. The consumer can see the difference in thickness, which can be interpreted as a difference in absorbency, between the secondary absorbent member 18 and the withdrawal member 20, visible through the transparent region 38 or protruding beyond the end of the applicator 12. Further, a perceptible view of the withdrawal member 20 and its location to the secondary member 18 can aid in post use removal of the tampon. Upon the time of removal, the consumer knows that the withdrawal member 20 is located adjacent to the secondary member 18 and that the withdrawal member is different from the secondary member. Further, having the ability to view both the secondary absorbent member and the withdrawal member offers reassurance that the tampon is configured properly, all parts are adequately connected, and that the tampon is ready for insertion by seeing each part of the tampon elongated.

Further to the above, the withdrawal member 20 can extend beyond the end of the plunger 24 such that a portion of the withdrawal member 20 is external of the applicator 12. The withdrawal member 20 can comprise one or more colors such that a consumer can have a first visual impression of the withdrawal member 20 through a transparent region 38 of the applicator 12 and a second visual impression of the withdrawal member 20 externally of the applicator 12. For example, in one embodiment, the withdrawal member 20 can comprise a third tampon color being yellow and a fourth tampon color being blue. A consumer could then view the third tampon color of the withdrawal member 20 through a transparent region 38 of the applicator 12 and the fourth tampon color of the withdrawal member 20 externally of the applicator 12. Similar to the above, one of ordinary skill in the art would readily recognize that any member of the tampon 14 can comprise one or more colors. For example, the secondary absorbent member 18 can comprise the colors blue and purple and/or the primary absorbent member 16 can comprise white and orange.

As previously stated, the plunger 24 can also comprise an opaque region 68. Thus, the withdrawal member 20 located in the opaque region 68 cannot be visually perceived. The opaque region 68 of the plunger 24 can comprise a second applicator color. The second applicator color can be the same as the second tampon color of the secondary absorbent member 18 and the first applicator color of the insertion portion 22. For example, in one embodiment, all of the first applicator color, second tampon color, and second applicator color can be purple, and the first tampon color of the primary absorbent member 16 and the third tampon color of the withdrawal member 20 can be a color other than purple. The configuration of this embodiment and similar embodiments gives consumers a signal that the hygiene device is ready for use. More specifically, a consumer of a hygiene device, as previously described, would be able to perceive the purple insertion portion followed by the purple secondary absorbent member followed by the purple opaque region of the plunger. This use of color signals to the consumer that the tampon 14 is appropriately housed within the applicator and is in a position to be inserted. The continuum of the same color is a signal to consumer that the tampon is ready for use.

Referring to FIG. 9, one or more of the above disclosed hygiene devices 10 (for example, as shown in FIG. 1) can be combined in a package 70. The package 70 can comprise one or more walls 76. The one or more walls 76 can surround at least a first hygiene device and a second hygiene device (not shown). In one example embodiment, the first hygiene device can comprise a first tampon that comprises a primary absorbent member and a secondary absorbent member. As previously described, the primary absorbent member can comprise a leading end and a trailing end opposite the leading end, and an intermediate region between the trailing end and the leading end. Similarly, the secondary absorbent member can be adjacent to the trailing end of the primary absorbent member. Further, the secondary absorbent member can comprise a first color. The first hygiene device, which can be a first tampon, can be housed within a first applicator, as previously disclosed. The first applicator can comprise an insertion portion and a plunger operatively engaged with the insertion portion. Further, the plunger can comprise a first transparent region so that the secondary absorbent member is visually perceptible through the transparent region. The visually perceptible secondary absorbent member creates a first visual impression for the consumer. As stated, the package can comprise a first hygiene device and a second hygiene device. The second hygiene device can comprise a second tampon that comprises a primary absorbent member and a secondary absorbent member. The primary absorbent member can comprise a leading end and a trailing end opposite the leading end, and an intermediate region between the trailing end and the leading end. The secondary absorbent member can be adjacent to the trailing end of the primary absorbent member. The secondary absorbent member can comprise a second tampon color. Further, the second hygiene device, which can be a second tampon, can be housed in a second applicator that can be configured to dispense the tampon. The second applicator can comprise an insertion portion and a plunger operatively engaged with the insertion portion. The plunger can comprise a second transparent region, wherein the secondary absorbent member is visually perceptible through the second transparent region. This creates a second visual impression for the consumer. The first tampon color can be different than or the same as the second tampon color. Further, the first visual impression can be different than or the same as the second visual impression. Both the first transparent region and the second transparent region can be at least one of clear and a color. For example, the first transparent region can be the color purple and the second transparent region can be clear.

For example, the first hygiene device can comprise a first tampon comprising primary absorbent member that is white and a secondary absorbent member that is blue. Further, the second hygiene device can comprise a second tampon comprising a primary absorbent member this is white and a secondary absorbent member that is pink. Thus, the first tampon color is blue and the second tampon color is pink. Accordingly, the first visual impression is different from the second visual impression.

In another example embodiment, either one of or both of the first hygiene device and the second hygiene device can further comprise a withdrawal member. The withdrawal member can be disposed on at least one of the primary absorbent member or the secondary absorbent member. The primary absorbent member of the first tampon can comprise a third tampon color and the withdrawal member of the first tampon can comprise a fourth tampon color. Similarly, the primary absorbent member of the second tampon can comprise a fifth tampon color and the withdrawal member of the second tampon can comprise a sixth tampon color. Any one of the first, second, third, fourth, fifth, or sixth tampon colors can be the same or different. Further, any portion of the first tampon and any portion of the second tampon can comprise additional colors such that the withdrawal member comprises two colors, such as white and blue. The virtually infinite number of color combinations across the various members of the tampon can allow the manufacturers to provide tampons that not only point to the functional features of the device, such as absorbency, but also provide a sense of enjoyment to the consumer. Most often, a women's menstrual cycle causes pain, fatigue, mood swings, and other discomforting side effects. Thus, manufacturers look for ways to provide some delight and happiness to consumers while using their products. Having a package with multiple different types of hygiene devices having several color combinations allows women to experience a sense of surprise and enjoyment when opening the hygiene device. Each package can be designed with hygiene devices that differ in color combinations. Thus, this "fortune cookie" type package provides a benefit to both manufacturers and consumers.

In yet another embodiment, the first tampon and the second tampon can differ by absorbency. Thus, the first tampon and the second tampon can differ by at least one of color and absorbency. As such, the first tampon can comprise a primary absorbent member having a first absorbency and/or a secondary absorbent member having a second absorbency and/or a withdrawal member having a third absorbency. Similarly, the second tampon can a primary absorbent member having a fourth absorbency and/or a secondary absorbent member having a fifth absorbency, and/or a withdrawal member having a sixth absorbency. In the first tampon, the first absorbency can be greater than at least one of the second absorbency and the third absorbency. In the second tampon, the fourth absorbency can be greater than the fifth absorbency and the sixth absorbency. Further, the first absorbency of the primary absorbent member of the first tampon can be greater than, less than, or the same as the fourth absorbency of the primary absorbent member of the second tampon. The second absorbency of the secondary absorbent member of the first tampon can be greater than, less than, or the same as the fifth absorbency of the secondary absorbent member of the second tampon.

Further to the above, color can be used to indicate absorbency. More specifically, a package can comprise a first tampon and a second tampon comprising the color green and a third tampon and a fourth tampon comprising the color yellow. The first tampon and the second can have substantially the same absorbency and the third tampon and the fourth tampon can have substantially the same absorbency. Substantially the same absorbency means that the two absorbency values are within about 10% of one another and/or as identified by one of ordinary skill in the art to be within the same predefined absorbency range, which may be dictated by a regulatory agency. More specifically, the first tampon and the second tampon can each comprise a secondary absorbent member being a color green. The third tampon and the fourth tampon can each comprise a secondary absorbent member being a color yellow. Further, the absorbency of the first and second tampons can be greater than that of the third and fourth tampons. Thus, the color green on a tampon can indicate to a consumer an absorbency greater than a tampon having the color yellow. This color and absorbency combination allows the manufacturer to communicate to consumers through visual perception the absorbency of the tampons and how each tampon can have a different level of absorbency. In addition, the color can provide an additional indication that the correct consumer product is being used. For example, a tampon having a greater absorbency can be used for higher flow times and having a consistent color indicating greater absorbency can allow consumers to readily identify the correct absorbency. This added visual impression provides users another degree of assurance and comfort in using the hygiene device. One of skill in the art would readily recognize that various colors can be used to indicate absorbency and to distinguish between different levels of absorbency.

In yet another embodiment, the package of one or more hygiene devices can comprise a first hygiene device and a second hygiene device. The first hygiene device can comprise a first tampon. The first tampon can comprise a primary absorbent member comprising a leading end and a trailing end opposite the leading end, and an intermediate region between the trailing end and the leading end, and a withdrawal member disposed on the primary absorbent member. The withdrawal member can comprise at least a first tampon color. One of ordinary skill in the art would recognize that the withdrawal member can be more than one color. The first tampon can be housed within a first applicator. The first applicator is configured to dispense the first tampon at the time of use. The first applicator can comprise an insertion portion and a plunger. The plunger can be operatively engaged with the insertion portion. The plunger can comprise a first transparent region that can allow the withdrawal member to be visually perceptible in the first applicator. This can create a first visual impression. Further, the second hygiene device can be a second tampon. The second tampon can comprise a primary absorbent member comprising a leading end and a trailing end opposite the leading end, and an intermediate region between the trailing end and the leading end. The second tampon can further comprise a withdrawal member disposed on the primary absorbent member. The withdrawal member can have at least a second tampon color. One of ordinary skill in the art would recognize that the withdrawal member can comprise more than one color. The second tampon can be housed within a second applicator configured to dispense the second tampon at the time of use. The second applicator can comprise an insertion portion operatively engaged with a plunger. The plunger can comprise a second transparent region. The second transparent region allows the withdrawal member of the second tampon to be visually perceptible through the second applicator. The second transparent region creates a second visual impression. The first tampon color can be the same or different than the second tampon color. Similarly, the first visual impression can be the same or different from the second visual impression.

In another embodiment, the first tampon can also comprise a secondary absorbent member adjacent to the trailing end of the primary absorbent member of the first tampon. By "adjacent" it is meant that the secondary absorbent member can physically abut the primary absorbent member, as shown in FIG. 2, or it does not physically abut but rather is in close proximity to the primary absorbent member (not shown). The secondary absorbent member of the first tampon can comprise a third tampon color. The third tampon color can be different than or the same as the first tampon color. In addition, the second tampon can comprise a secondary absorbent member adjacent to the trailing end of the primary absorbent member of the second tampon. The secondary absorbent member of the second tampon comprises a fourth tampon color. The fourth tampon color can be the same as or different from the second tampon color.

The first applicator can comprise a first applicator color. The first applicator color can be the same as or different than the first tampon color. Also, the second applicator can comprise a second applicator color. The second applicator color can be the same as or different than the second tampon color.

In yet another embodiment, the first applicator can comprise an insertion portion comprising a first transparent region, and a plunger operatively engaged with the insertion portion. The plunger can comprise a second transparent region. Thus, the secondary absorbent member of the first tampon can be visually perceptible through at least one of the first transparent region and the second transparent region creating a first visual impression. Similarly, a second applicator can comprise an insertion portion and a plunger operatively engaged with the insertion portion. The insertion portion can comprise a third transparent region and the plunger can comprise a fourth transparent region. The secondary absorbent member can be visually perceptible through at least one of the third transparent region and the fourth transparent region creating a second visual impression. The first visual impression can be the same or different than the second visual impression. Further, the first applicator can have a first applicator color and the second applicator can have a second applicator color. The first applicator color and the second applicator color can be the same or different. Additionally, any color of the first tampon can be the same or different than the first applicator color, and any color of the second tampon can be the same or different than the second applicator color.

Each hygiene device can comprise an individual wrap (not shown) that seals the device. More specifically, each hygiene device comprising an applicator housing a tampon can comprise a wrap, such as a sealed overwrap that contains the hygiene device prior to use. The wrap can comprise a transparent region such that at least a portion of the hygiene device is visually perceptible within the wrap. Further, the wrap can be made of a flexible material and/or a rigid material. For example, the wrap can be made of plastic, paper, or cardboard. Having a wrap that permits the consumer to visually perceive the hygiene device allows the consumer to immediately perceive the characteristics of the applicator and tampon.

The package 70 can also comprise one or more indicia 74. The indicia 74 can be any brand name, graphic, illustration, or other information concerning the product. In one example embodiment, the indicia 74 can be directed to the secondary absorbent member and can also include instructions or information pertaining to the absorbency and plurality of colors of the secondary absorbent member. In another example, the indicia 74 can be directed to the array of applicator colors and/or the combination of applicator and tampon colors contained in the package 70.

The package 70 can be made of a flexible material and/or a rigid material. More specifically, the walls 76 can be made of a flexible material and/or a rigid material. For example, the package can be made of plastic, paper, or cardboard. In yet an alternative embodiment, the package 70 can be made of a combination of flexible and rigid materials. Further, the package 70 can comprise one or more windows 72 through which one or more hygiene devices are visible at the time of purchase. The one or more windows 72 can comprise transparent regions 38 such that one or more hygiene devices can be seen from the exterior of the package 70. Similar to the above, the transparent regions 38 can be clear or the transparent regions 38 can comprise a window color.

As previously disclosed, a pessary refers to any type of substantially non-absorbent structure for the purpose of reducing urine leakage and/or supporting a prolapsed uterus and/or bladder. Substantially non-absorbent means that the structure absorbs less than about 10% of the fluid that comes into contact with the pessary. The above disclosure can also apply to a hygiene device that is a pessary. More specifically, a pessary can comprise a compressive member that can correlate structurally to the primary absorbent member, an optional secondary member which can correlate structurally to the secondary absorbent member, and a withdrawal member, wherein each member is made from a non-absorbent material, such as a polymer, or a material rendered hydrophobic by one or more additives. Similar to the above, the pessary can comprise one or more colors and be housed within an applicator. The applicator can comprise one or more transparent regions and/or opaque regions such that a consumer can visually perceive at least a portion of the pessary housed within the applicator. Still further, the pessary and applicator can each comprise various color combination similar to those previously disclosed with respect to tampons and tampon applicators.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hygiene device comprising:
   a tampon comprising:
      a primary absorbent member comprising a leading end and a trailing end opposite the leading end, and an intermediate region between the trailing end and the leading end, wherein the primary absorbent member comprises a first tampon color and a first cross sectional area;
      a secondary absorbent member that is mechanically tied to the primary absorbent member, wherein the secondary absorbent member comprises a second tampon color and a second cross sectional area, and wherein the first cross sectional area is greater than the second cross sectional area;
      a withdrawal member disposed on at least one of the secondary absorbent member and the primary absorbent member and extending from the secondary absorbent member in a direction substantially parallel to a longitudinal tampon axis, wherein the withdrawal member comprises a third tampon color; and
   an applicator housing the tampon, the applicator comprising:
      an insertion portion that includes an opaque region;
      a plunger operatively engaged with the insertion portion, the plunger comprising:
         a first component comprising a transparent region sized such that both of the secondary absorbent member and the withdrawal member are visually perceptible through the first component;
         a second component slidably engaged with the first component, and wherein the first component comprises a lip, wherein the second component comprises a projection capable of engaging the lip such that the first component and the second component may be removably locked to one another.

2. The hygiene device of claim 1, wherein the first tampon color is the same as at least one of the second tampon color and the third tampon color.

3. The hygiene device of claim 1, wherein the second tampon color is different from the third tampon color.

4. The hygiene device of claim 1, wherein the first tampon color is different from at least one of the second tampon color and the third tampon color.

5. The hygiene device of claim 1, wherein the insertion portion comprises a first applicator color and the plunger comprises a second applicator color.

6. The hygiene device of claim 5, wherein the second tampon color of the secondary absorbent member is the same as at least one of the first applicator color and the second applicator color.

7. The hygiene device of claim 5, wherein the first applicator color is different from the second applicator color.

8. The hygiene device of claim 1, wherein the second component comprises an opaque region.

9. The hygiene device of claim 1, wherein the transparent region comprises a color, and wherein the withdrawal member that is visually perceptible through the first component creates a first visual impression and a portion of the withdrawal member external of the applicator creates a second visual impression, and wherein the first visual impression is different from the second visual impression.

10. A hygiene device comprising:
    a tampon comprising:
       a primary absorbent member comprising a leading end and a trailing end opposite the leading end, an intermediate region between the trailing end and the leading end and a first cross sectional area;
       a secondary absorbent member that is mechanically tied to the trailing end of the primary absorbent member and a second cross sectional area, and wherein the first cross sectional area is greater than the second cross sectional area;
       a withdrawal member disposed on at least one of the secondary absorbent member and the primary absorbent member; and
    an applicator housing the tampon, the applicator comprising:
       an insertion portion that includes an opaque portion;
       a plunger operatively engaged with the insertion portion wherein the plunger comprises a transparent region configured to allow visual perception of at least a portion of the secondary absorbent member though the plunger, and an opaque region slidably engaged with the transparent region, wherein the transparent region comprises a lip, wherein the opaque region comprises a projection capable of engaging the lip such that the transparent region and the opaque region may be removably locked to one another.

11. The hygiene device of claim 10, wherein the primary absorbent region comprises a first tampon color, the secondary absorbent member comprises a second tampon color, and the withdrawal member comprises a third tampon color.

12. The hygiene device of claim 10, wherein the insertion portion comprises a first applicator color, and the first applicator color is the same as the second tampon color of the secondary absorbent member.

13. The hygiene device of claim 11, wherein the first tampon color is the same as at least one of the second tampon color and the third tampon color.

14. The hygiene device of claim 10, wherein the transparent region comprises a second applicator color, and wherein the second applicator color is different from the second tampon color of the secondary absorbent member.

15. The hygiene device of claim 10, wherein the opaque region comprises a third applicator color, and wherein the insertion portion comprises a first applicator color, and wherein the first applicator color is the same as the third applicator color.

* * * * *